(12) United States Patent  
Lemire et al.

(10) Patent No.: US 6,699,383 B2  
(45) Date of Patent: Mar. 2, 2004

(54) METHOD FOR DETERMINING A NOX CONCENTRATION

(75) Inventors: Bertrand Lemire, Schierling (DE); Tim Walde, Regensburg (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/156,483

(22) Filed: May 28, 2002

(65) Prior Publication Data

US 2002/0179458 A1 Dec. 5, 2002

Related U.S. Application Data

(63) Continuation of application No. PCT/DE00/04128, filed on Nov. 22, 2000.

(30) Foreign Application Priority Data

Nov. 25, 1999 (DE) ......................................... 199 56 822

(51) Int. Cl.$^7$ ............................................. G01N 27/407
(52) U.S. Cl. .................. 205/781; 205/784.5; 736/23.31
(58) Field of Search ............................. 205/781, 783.5, 205/784, 784.5; 204/425, 426; 73/23.31, 23.32

(56) References Cited

U.S. PATENT DOCUMENTS

| | | | |
|---|---|---|---|
| 5,736,028 A | | 4/1998 | Hjortsberg et al. |
| 5,780,710 A | * | 7/1998 | Murase et al. ............... 73/1.06 |
| 6,082,176 A | * | 7/2000 | Kondo et al. ............... 73/23.31 |

FOREIGN PATENT DOCUMENTS

| | | |
|---|---|---|
| EP | 0 810 430 A2 | 12/1997 |
| EP | 0 859 232 A2 | 8/1998 |
| EP | 0 878 709 A2 * | 11/1998 |

OTHER PUBLICATIONS

Wiedenmann et al "Automotive Electronics Handbook", Chapter 6 "Exhaust Gas Sensors", pp. 6.1–6.23, 1995.*
"Thick Film ZrO2NOx Sensor for the Measuremen of Low NOx Concentration" (Kato et al.), Society of Automotive Engineers, Publication 980170, 1998, pp. 69–77.
"Performance of Thick Film NOx Sensor on Diesel and Gasoline Engines" (Kato et al.), Society of Automotive Engineers, Publication 97058, 1997, pp. 199–206.

* cited by examiner

Primary Examiner—Kaj K. Olsen  
(74) Attorney, Agent, or Firm—Laurence A. Greenberg; Werner H. Stemer; Ralph E. Locher

(57) ABSTRACT

A thick-film measurement sensor includes two measurement cells and is used to measure the NOx concentration in the exhaust gas from an internal combustion engine. The $1/\lambda$ value of the exhaust gas is determined from an oxygen ion pump current flowing in the first measurement cell, for example, by a characteristic diagram, and, a measurement error, which can be used to correct the measured NOx concentration, is determined from this $1/\lambda$ value, for example, by a characteristic curve that has previously been determined in a calibration measurement. The invention is based on the discovery that the measurement error is dependent on the air ratio in the exhaust gas. If this is expressed by the $1/\lambda$ value, there is no need for a complex division calculation during the correction.

5 Claims, 2 Drawing Sheets

US 6,699,383 B2

METHOD FOR DETERMINING A NOX CONCENTRATION

CROSS-REFERENCE TO RELATED APPLICATION

This application is a continuation of International Application PCT/DE00/04128, filed Nov. 22, 2000, which designated the United States and was not published in English.

BACKGROUND OF THE INVENTION

Field of the Invention:

The invention relates to a method for determining the NOx concentration in the exhaust gas from an internal combustion engine.

To measure the NOx concentration in a gas, for example, in the exhaust gas from an internal combustion engine, prior art devices use a thick-film measurement sensor. Such a measurement sensor is described, for example, in the publication N. Kato et al., "Thick Film $ZrO_2$ NOx Sensor for the Measurement of Low NOx Concentration", Society of Automotive Engineers, publication 980170, 1989, or in N. Kato et al., "Performance of Thick Film NOx Sensor on Diesel and Gasoline Engines", Society of Automotive Engineers, publication 970858, 1997. The measurement sensor has two measurement cells and includes a zirconium oxide that conducts oxygen ions. It implements the following measurement concept: in a first measurement cell, to which the gas that is to be measured is supplied through a diffusion barrier, a first oxygen ion pump current is used to establish a first oxygen concentration, during which process there should be no decomposition of NOx. In a second measurement cell, which is connected to the first through a diffusion barrier, the oxygen content is reduced further by a second oxygen ion pump current. The decomposition of NOx at a measurement electrode leads to a third oxygen ion pump current, which is a measure of the NOx concentration. The entire measurement sensor is brought to an elevated temperature by an electrical heater, e.g., to 750° C.

During the measurement of the NOx concentration, a deviation from the true NOx concentration arises because the NOx measured value is distorted as a result of slippage of oxygen from the first chamber into the second chamber. Although pumping the oxygen slippage in the second cell out reduces the oxygen content distorting the measurement signal considerably, it does not do so completely because oxygen that originates from the decomposition of NOx is still also recorded.

SUMMARY OF THE INVENTION

It is accordingly an object of the invention to provide a method for determining a NOx concentration that overcomes the hereinafore-mentioned disadvantages of the heretofore-known devices and methods of this general type and that records a NOx concentration in the exhaust gas of an internal combustion engine using a measurement sensor in a more accurate way.

With the foregoing and other objects in view, there is provided, in accordance with the invention, a method for determining the NOx concentration in an exhaust gas from an internal combustion engine including the steps of introducing some of the exhaust gas into a first measurement cell of a measurement sensor and establishing a first oxygen concentration in the first measurement cell through an oxygen ion pump current, establishing a second oxygen concentration in a second measurement cell connected to the first measurement cell, measuring the NOx concentration in the second measurement cell, determining from the oxygen ion pump current an air ratio signal representing a function of a $\lambda$ value of the exhaust gas, determining from the air ratio signal a measurement error representing a deviation of the measured NOx concentration from a true NOx concentration, and correcting the measured NOx concentration with the measurement error.

The invention is based on the discovery that the measurement error in the value for the NOx concentration supplied by a NOx measurement sensor that is of two-chamber structure is dependent on the level of the oxygen concentration in the exhaust gas from an internal combustion engine. The measurement sensor cannot measure the oxygen concentration. The first oxygen ion pump current, however, is a direct measure of the air ratio $\lambda$ of the exhaust gas. If the measurement error is now related not to the oxygen concentration, but rather to $\lambda$, preferably to its reciprocal $1/\lambda$, it is found that the measurement error for many measurement sensors can be described by a simple function, and even substantially linearly for $1/\lambda$. The term substantially linearly is understood as meaning that, when developing a series of higher-order terms it is only necessary to take account of very low coefficients.

Therefore, an air ratio signal, preferably the $1/\lambda$ value of the exhaust gas, is obtained from the first oxygen ion pump current in the first measurement cell, and, by such a signal, the measurement error is determined by using a relationship between air ratio signal and measurement error. The measured NOx concentration is then corrected by the measurement error.

The relationship is preferably determined in advance in a calibration measurement so that the measurement error is in the form of a characteristic diagram, a characteristic curve, or a functional relationship.

In accordance with another mode of the invention, a relationship between the air ratio signal and the measurement error is determined in a calibration measurement by exposing the measurement sensor to various gas mixtures, recording the measurement error and describing the measurement error as a characteristic diagram, a characteristic curve, or a functional relationship, and varying at least the $\lambda$ value and the NOx concentration in the gas mixtures.

In accordance with a further mode of the invention, the correction step is carried out by correcting with multiplication/addition calculation operations and/or subtraction calculation operations.

In accordance with an added mode of the invention, the measurement error determining step is carried out by applying a substantially linear function as a relationship between the air ratio signal and the measurement error.

To be able to obtain the air ratio signal from the first oxygen ion pump current, a characteristic curve, which represents the relationship between first oxygen ion pump current in the first cell and the air ratio signal, for example $1/\lambda$ or another function of $\lambda$, is also determined. In such a case, the relationship between first oxygen ion pump current and $1/\lambda$ is, surprisingly, substantially linear, so that it is furthermore advantageous to select $1/\lambda$ as the air ratio signal.

In accordance with an additional mode of the invention, a characteristic curve or a characteristic diagram is used to determine the air ratio signal from the oxygen ion pump current.

With the objects of the invention in view, there is also provided a method for determining the NOx concentration in an exhaust gas from an internal combustion engine including the steps of providing a measurement sensor having a first measurement cell and a second measurement cell connected to the first measurement cell, introducing some of the exhaust gas into the first measurement cell and establishing a first oxygen concentration in the first measurement cell through an oxygen ion pump current, establishing a second oxygen concentration in the second measurement cell, measuring the NOx concentration in the second measurement cell, determining from the oxygen ion pump current an air ratio signal representing a function of a λ value of the exhaust gas, determining from the air ratio signal a measurement error representing a deviation of the measured NOx concentration from a true NOx concentration, and correcting the measured NOx concentration with the measurement error.

The method according to the invention has the advantage that only multiplications, subtractions, and additions are required during the correction of the measured NOx concentration. A division, which would impose excessively high demands on the calculation ability of an inexpensive microcontroller, is not required.

Other features that are considered as characteristic for the invention are set forth in the appended claims.

Although the invention is illustrated and described herein as embodied in a method for determining the NOx concentration, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

DESCRIPTION OF THE PREFERRED EMBODIMENTS

Figure 1:
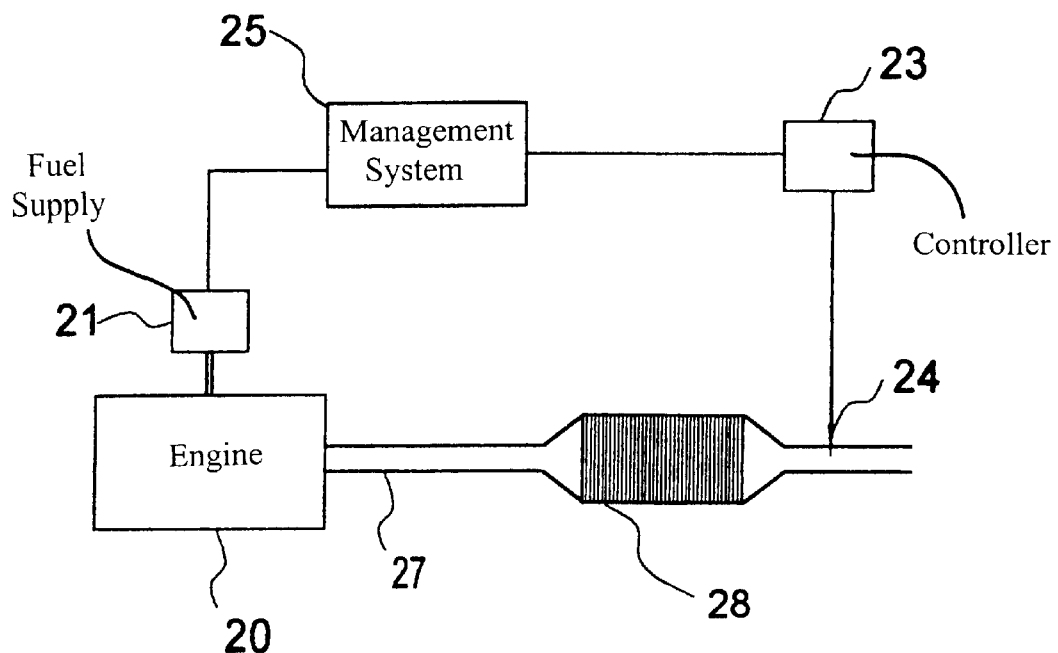
FIG. 1 is a block circuit diagram of a device for carrying out the method according to the invention.
Figure 2:
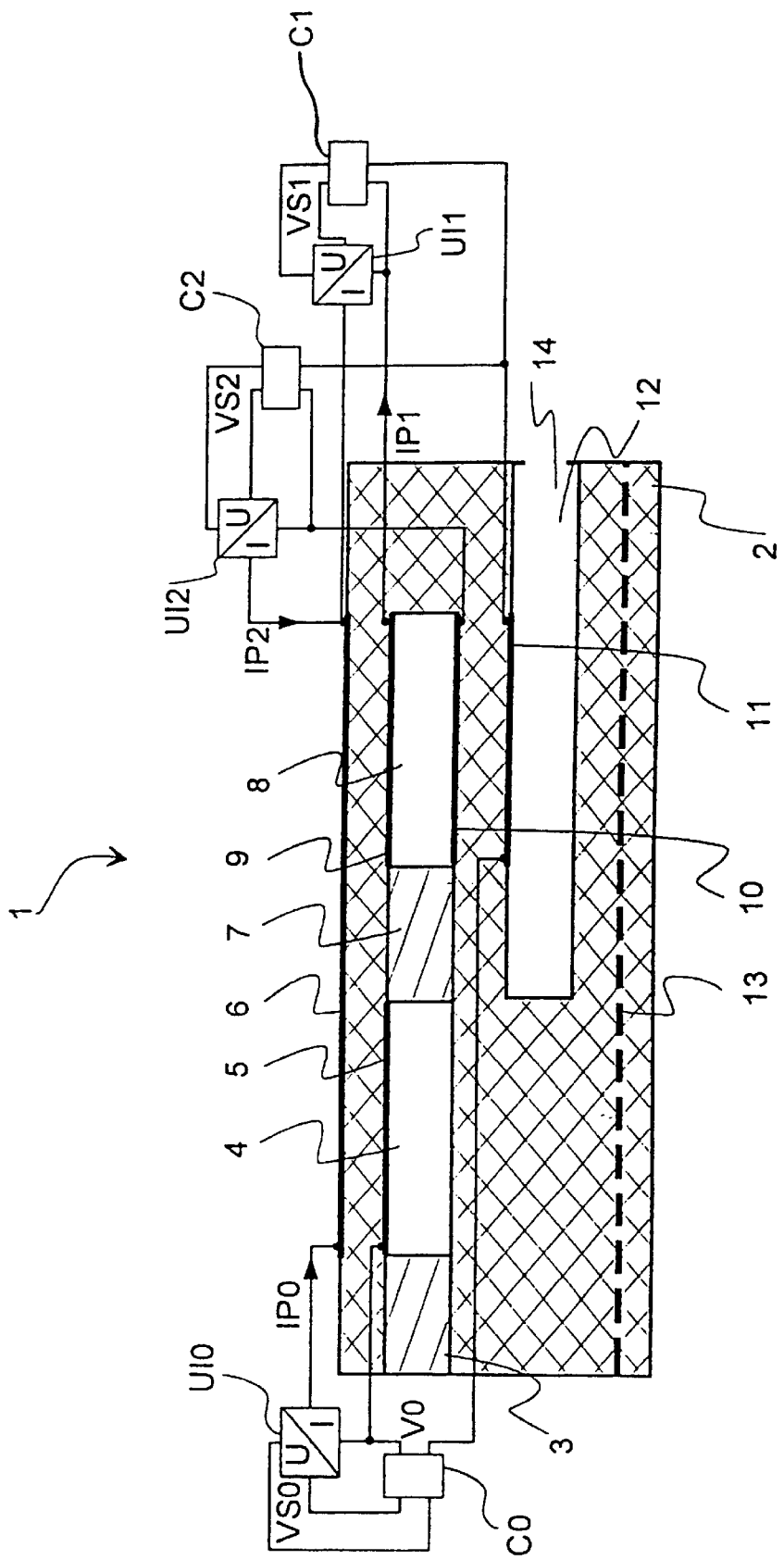
FIG. 2 is a block circuit diagram of a device for carrying out the method according to the invention and a cross-sectional view of a NOx measurement sensor according to the invention.

Referring now to the figures of the drawings in detail and first, particularly to FIG. 2 thereof, there is shown a section through a NOx measurement sensor 1. In the device illustrated in FIG. 1, the measurement sensor 1 is used as measurement sensor 24 for determining the NOx concentration in the exhaust section 27 of an internal combustion engine 20. For such a purpose, a control unit 23 reads out the measured values from the NOx measurement sensor 24. The control unit 23 is connected to the NOx measurement sensor 24, and fed to an engine management system 25 of the internal combustion engine 20. The engine management system 25 controls a fuel supply system 21 of the internal combustion engine 20 such that an NOx-reducing catalytic converter 28, which, in this case, lies upstream of the NOx measurement sensor 24 in the exhaust section 27 of the internal combustion engine 20, has optimum operating characteristics.

The measurement sensor 24, 1 is illustrated in more detail in FIG. 2. The measurement sensor 1, which includes a solid electrolyte 2, in this case $ZrO_2$, receives the exhaust gas that is to be measured and the NOx concentration of which is to be determined, through a diffusion barrier 3. The exhaust gas diffuses through the diffusion barrier 3 into a first measurement cell 4. The oxygen content in the measurement cell 4 is measured by tapping a Nernst voltage between a first electrode 5 and a reference electrode 11 that is exposed to ambient air. The reference electrode 11 is disposed in an air passage 12, into which ambient air passes through an opening 14.

The Nernst voltage that is tapped is fed to an 8-bit microcontroller, which is used as controller C0 and provides a control voltage VS0. The voltage VS0 actuates a voltage-controlled current source UI0 that drives a first oxygen ion pump current IP0 through the solid electrolyte 2 of the measurement sensor 1 between the first electrode 5 and an external electrode 6. The control voltage VS0 from the controller C0 in the first measurement cell 4 is used to set a predetermined oxygen concentration. This is measured through the Nernst voltage between the electrode 5 and the reference electrode 11, so that the control circuit of the controller C0 is closed. The first oxygen ion pump current is a measure of the air ratio in the exhaust gas, as exists from lambda sensors.

Therefore, the circuit configuration described establishes a predetermined oxygen concentration in the first measurement cell 4. The second measurement cell 8 is connected to the first measurement cell 4 through a further diffusion barrier 7. The gas that is present in the first measurement cell 4 diffuses through the diffusion barrier 7 into the second measurement cell 8. A second oxygen concentration is established in the second measurement cell 8 by a circuit configuration. For such a purpose, a second Nernst voltage is tapped off between a second electrode 9 and the reference electrode 11 and is fed to a controller C1, which provides a second control voltage VS1 that is used to actuate a second voltage-control current source UI1. The circuit configuration for driving the oxygen ion pump current IP1 from the second measurement cell 8, therefore, corresponds to the circuit configuration for the first measurement cell 4.

The circuit configuration drives the oxygen ion pump current IP1 such that a predetermined oxygen concentration is established in the second measurement cell 8.

The oxygen concentration is selected such that NOx is not affected by the operations that take place, and, in particular, there is no decomposition. At the measurement electrode 10, which may be a catalytic, the NOx is then pumped, in a third oxygen ion pump current IP2, from the measurement electrode 10 to the external electrode 6. Because the residual oxygen content in the measurement cell 8 has fallen sufficiently, the third oxygen ion pump current IP2 is carried substantially only by oxygen ions that originate from the decomposition of NOx at the measurement electrode 10. The pump current IP2 is, therefore, a measure of the NOx concentration in the measurement cell 8 and, therefore, in the exhaust gas that is to be measured.

The pump current IP2, like the previous pump currents, is driven by a voltage-controlled current source UI2, the control voltage VS2 of which is predetermined by a controller C2, which taps the Nernst voltage between the measurement electrode 10 and the reference electrode 11 and sets a predetermined Nernst voltage by stipulating the control voltage VS2.

However, the residual oxygen content in the measurement cell 8 is only ideally zero because slippage of oxygen from the first measurement cell into the second measurement cell means that the measured NOx concentration is still always dependent on the oxygen concentration in the exhaust gas.

Figure 3:
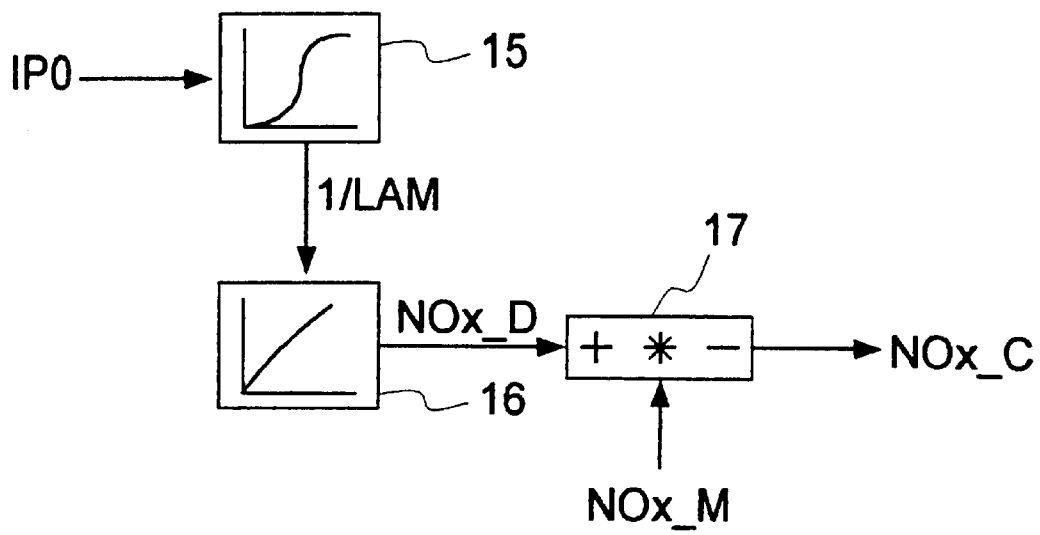
FIG. 3 is a block circuit flow diagram for carrying out the method according to the invention.

Such a dependent relationship is now corrected by calculation using the method that is diagrammatically illustrated in FIG. 3.

First of all, an oxygen signal 1/LAM, which expresses the air ratio in the exhaust gas, is obtained from the first oxygen ion pump current IP0 in the first measurement cell 4. The first oxygen ion pump current IP0 is, in this case, converted using a characteristic curve 15 or a characteristic diagram that assigns each current an $1/\lambda$ value, which, in this case, is the air ratio signal 1/LAM. The characteristic curve was previously determined for the corresponding measurement sensor 1 in a calibration measurement.

This air ratio signal 1/LAM is converted into a measurement error NOx_D using a further characteristic curve 16. The characteristic curve 16 was obtained from a corresponding calibration measurement of the measurement sensor 1 and expresses the relationship between measurement error and 1/LAM.

If it is possible to find a functional relationship between measurement error NOx_D and air ratio signal 1/LAM, the conversion by characteristic curve is replaced by calculation by using a functional relationship. If the $1/\lambda$ value is taken as the air ratio signal, a substantially linear relationship results. If it is impossible to rely on a substantially linear relationship of this type, the characteristic curve 16 is stored instead of a function. However, in the text that follows it is assumed that the $1/\lambda$ value is used as air ratio signal 1/LAM, and, therefore, it is possible to rely on a substantially linear relationship. Then, by simple multiplication of the value of the air ratio signal 1/LAM by a multiplication factor and addition of an addition factor makes it possible to obtain a measurement error NOx_D. By simply multiplying the measurement error NOx_D, which is then realized, for example, as a correction multiplier, by the measured NOx concentration NOx_M in the calculation operation 17, the corrected NOx concentration NOx_C is obtained.

Neither the determination of the measurement error NOx_D from the air ratio signal 1/LAM nor the calculation of the corrected NOx concentration NOx_C requires a division step, which would generally entail floating-point arithmetic and would, therefore, require a complex microcontroller. Instead, it is possible to use a simple, inexpensive microcontroller.

If it is not possible to rely on a substantially linear relationship when determining the measurement error NOx_D from the air ratio signal 1/LAM, but rather a characteristic curve 16 is used, the characteristic curve 15 can be combined with the characteristic curve 16, so that the measurement error NOx_D is obtained directly from the first oxygen ion pump current IP0, for example, as a multiplication or addition correction factor. This eliminates one working step because the generation of the air ratio signal 1/LAM is dispensed with. However, if the air ratio signal 1/LAM is required, for example, for other control functions during operation of the internal combustion engine, it may, of course, nevertheless, still be generated from the first oxygen ion pump current IP0.

We claim:

1. A method for determining the NOx concentration in an exhaust gas from an internal combustion engine, which comprises:

introducing some of the exhaust gas into a first measurement cell of a measurement sensor and establishing a first oxygen concentration in the first measurement cell through a first oxygen ion pump current;

establishing a second reduced oxygen concentration in a second measurement cell through a second oxygen pump current, the second measurement cell being connected to the first measurement cell;

measuring the NOx concentration by a third oxygen pump current from the second measurement cell;

determining from the first oxygen ion pump current an air ratio signal representing a function of a $\lambda$ value of the exhaust gas;

determining from the air ratio signal a measurement error representing a deviation of the measured NOx concentration from a true NOx concentration; and correcting the measured NOx concentration with the measurement error.

2. The method according to claim 1, which further comprises:

determining a substantially linear relationship between $1/\lambda$ and the measurement error in a calibration measurement by:

exposing the measurement sensor to various gas mixtures;

recording the measurement error and describing the measurement error as one of:

a characteristic diagram;

a characteristic curve; and a functional relationship; and varying at least the $\lambda$ value and the NOx concentration in the gas mixtures.

3. The method according to claim 1, which further comprises carrying out the correction step by correcting with at least one of multiplication/addition calculation operations and subtraction calculation operations.

4. The method according to claim 1, which further comprises using a $1/\lambda$ value as the air ratio signal and carrying out the measurement error determining step by applying a substantially linear relationship between the $1/\lambda$ value and the measurement error.

5. The method according to claim 1, which further comprises using one of a characteristic curve and a characteristic diagram to determine the air ratio signal from the oxygen ion pump current.

* * * * *